United States Patent
Foerster et al.

(10) Patent No.: US 6,255,253 B1
(45) Date of Patent: Jul. 3, 2001

(54) MICROEMULSIONS

(75) Inventors: Thomas Foerster, Erkrath; Marcus Claas, Hilden; Horst-Werner Wollenweber, Duesseldorf, all of (DE)

(73) Assignee: Cognis Deutschland GmbH, Duesseldorf (DE)

( * ) Notice: Subject to any disclaimer, the term of this patent is extended or adjusted under 35 U.S.C. 154(b) by 0 days.

(21) Appl. No.: 09/485,900

(22) PCT Filed: Jun. 6, 2000

(86) PCT No.: PCT/EP98/05049

§ 371 Date: May 19, 2000

§ 102(e) Date: May 19, 2000

(87) PCT Pub. No.: WO99/08517

PCT Pub. Date: Feb. 25, 1999

(30) Foreign Application Priority Data

Aug. 18, 1997 (DE) .............................................. 197 35 790

(51) Int. Cl.$^7$ ................................................... A01N 25/04
(52) U.S. Cl. ............................................. 504/363; 514/939
(58) Field of Search .............................. 504/363; 514/939

(56) References Cited

U.S. PATENT DOCUMENTS

| | | | |
|---|---|---|---|
| H224 | 3/1987 | Malik et al. | 71/92 |
| 3,547,828 | 12/1970 | Mansfield et al. | 252/351 |
| 4,943,265 | 7/1990 | Schmitt et al. | 474/25 |
| 5,258,358 | 11/1993 | Kocur et al. | 504/205 |
| 5,783,692 | * 7/1998 | Kirby et al. | 424/405 |
| 5,795,978 | * 8/1998 | Ansmann et al. | 536/120 |

FOREIGN PATENT DOCUMENTS

| | | |
|---|---|---|
| 19 43 689 | 3/1970 | (DE) . |
| 38 27 543 | 3/1990 | (DE) . |
| 0 299 654 | 1/1989 | (EP) . |
| 0 511 611 | 11/1992 | (EP) . |
| 0 729 700 | 9/1996 | (EP) . |
| WO91/00010 | 1/1991 | (WO) . |
| WO93/22917 | 11/1993 | (WO) . |
| WO95/03881 | 2/1995 | (WO) . |
| WO95/28083 | 10/1995 | (WO) . |
| WO96/08150 | 3/1996 | (WO) . |
| WO96/34078 | 10/1996 | (WO) . |
| WO97/00609 | 1/1997 | (WO) . |

\* cited by examiner

*Primary Examiner*—S. Mark Clardy
(74) *Attorney, Agent, or Firm*—John E. Drach; Steven J. Trzaska

(57) ABSTRACT

An agrochemical microemulsion containing: (a) an alkyl (oligo)glycoside; and (b) an oil phase containing: (i) an organic water-insoluble solvent selected from the group consisting of N,N-dimethyl amides of $C_{8-22}$ fatty acids, glycerol $C_{8-22}$ fatty acid esters of natural or synthetic origin, dialkyl ether having a total of from 12 to 24 carbon atoms, monohydric primary alcohols having from 12 to 24 carbon atoms, and mixtures thereof; and (ii) an agrochemical, and wherein 80% of the microemulsion contains droplets between 10 and 100 nm in size.

18 Claims, No Drawings

MICROEMULSIONS

BACKGROUND OF THE INVENTION

This invention relates to liquid concentrates of water-insoluble agricultural chemicals (hereinafter referred to as agrochemicals) and to a process for producing these concentrates.

Agrochemicals such as, for example, biocides, herbicides, insecticides and even fertilizers contain organic compounds which are insoluble or poorly soluble in water. In order to convert these agrochemicals into a form in which they are easy to handle by the user, they are often marketed as concentrated solutions in suitable organic solvents, for example alkyl benzene. Before use, these solutions have to be further diluted to the required concentrations. However, the use of these organic solvents is undesirable for economic reasons and above all for ecological reasons. Accordingly, there is a need for water-based concentrates of the agrochemicals in question.

WO 95/28083 describes water-based surfactant mixtures containing an alkyl naphthalene sulfonate and alkyl (oligo) glycosides and at least one pesticide and optionally other agrochemicals. EP 511 611 B1 describes aqueous solutions of the herbicide glufosinate ammonium. It is also mentioned in the specification that the claimed solutions may also contain other water-insoluble constituents in emulsified form. However, only aqueous solutions of the herbicide are disclosed in the Examples.

The known water-based formulations often show performance-related disadvantages in practice. Thus, the emulsions can separate on dilution with water. This problem occurs in particular where electrolyte-containing water, for example tap water, is used for dilution because the salt ions can upset the hydrophilic/lipophilic balance of the emulsifiers at the water/oil interface. In addition, problems arise during storage at low temperatures, for example below 10° C., because in that case the emulsion often has to be rehomogenized before use.

Accordingly, the problem addressed by the present invention was to provide ecologically safe, low-temperature-stable aqueous emulsions of water-insoluble or substantially water-insoluble agrochemicals with virtually unlimited dilutability.

BRIEF SUMMARY OF THE INVENTION

It has been found that water-insoluble agrochemicals can be processed in the presence of selected emulsifier combinations to form microemulsions with the required properties.

Accordingly, the present invention relates to a liquid concentrate of an agrochemical in the form of a transparent oil-in-water microemulsion with a droplet size of essentially 10 to 100 nm which contains alkyl (oligo)glycosides corresponding to general formula (I):

$$R\text{—}O\text{—}[Z]_x \qquad (I)$$

in which R is an alkyl group containing 8 to 22 carbon atoms, Z is a sugar unit containing 5 or 6 carbon atoms and x is a number of 1 to 10, as emulsifiers and optionally other auxiliaries and additives, characterized in that the oil phase contains a water-insoluble agrochemical and optionally an organic water-insoluble solvent.

DETAILED DESCRIPTION OF THE INVENTION

The microemulsions described herein are emulsions of the oil-in-water type. They are optically isotropic, thermodynamically stable systems which contain water-insoluble oils, emulsifiers and water. The clear or transparent appearance of the microemulsions is attributable to the small droplet size of the dispersed oils which is essentially below 300 nm, i.e. more than 50% and preferably more than 80% of the droplets are below 300 nm in size, fine-droplet microemulsions brown-red in transmitted light and a shimmering blue in reflected light being present in the range from 100 to 300 nm and substantially optically clear microemulsions being present in the particularly preferred range of 10 to 100 nm. The optical impression of the clear transparency is particularly good when the transmissivity of the emulsion for light with a wave length of 650 nm is at least 85%. The microemulsions according to the invention are stable over a broad temperature range of 0 to 50° C.

The concentrates according to the invention contain as oil phase the water-insoluble agrochemical and, optionally, a suitable water-insoluble solvent for that agrochemical. The agrochemical concentrates according to the invention contain the oil phase, i.e. agrochemical, solvent and optionally other auxiliaries and additives soluble or dispersible in the oil phase, in quantities of preferably 10 to 50% by weight. In the context of the present invention, the emulsifier does not count as part of the oil phase. The function of the solvent is above all to simplify handling of the partly inhalation-toxic agrochemicals because they are easier to process in solution. However, it has also been found that the stability of the emulsions can be improved by selected solvents.

Agrochemicals in the context of the present invention are substances which may be used for plant protection, but also herbicides and fertilizers. Agrochemicals also include insecticides, acaricides, nematicides, pesticides and also repellents or rodenticides, sexual attractants, mammal and bird repellents and chemosterilants as described, for example, in Chemie der Pflanzenschutz- und Schädlingsbekämp-fungsmittel, Vol. 1, Editor: R. Wegler, Springer-Verlag Berlin, 1970 and in The Pesticide Manual, World Compendium: 8th Edition, The British Crop Protection Council, 1987. The agrochemicals are insoluble in water. In the context of the present invention, this means a solubility in water at room temperature (21° C.) of less than 10% by weight and preferably less than 5% by weight. Agrochemicals with a solubility in water of less than 1% by weight are preferred. The agrochemicals may be solid or liquid at room temperature.

The agrochemical concentrates may contain mixtures of water-insoluble agrochemicals in any quantity ratios. They may also contain water-soluble compounds. However, concentrates free from water-soluble agrochemicals are preferred.

The concentrates preferably contain insecticides, for example from the group of chlorinated hydrocarbons, for example hexachlorocyclohexane derivatives or cyclodiene derivatives, pyrethrines, pyrethroids, N-isobutyl amides of unsaturated $C_{8-22}$ fatty acids, carbamates or phosphoric acid esters. A preferred insecticide is nonanoic acid methyl ester. Other preferred agrochemicals are insect repellents, for example 3-(N-n-butyl-N-acetylamino)-propionic acid methyl ester, N,N-diethyl caprylic acid amide or diethyl-m-toluamide. In another preferred embodiment, water-insoluble biocides, fungicides, herbicides or pesticides are present as agrochemicals.

The concentrates contain the water-insoluble agrochemicals in quantities of preferably 10 to 40% by weight and more preferably 15 to 30% by weight.

The solvents insoluble in water at room temperature (i.e. solubility below 10% by weight) are preferably selected from esters of $C_{12-22}$ fatty acids and primary $C_{1-4}$ alcohols, N,N-dimethyl amides or $C_{8-22}$ fatty acids, monohydric primary alcohols containing 12 to 24 carbon atoms, glycerol-$C_{8-22}$-fatty acid esters of natural or synthetic origin and dialkyl ethers containing a total of 12 to 24 carbon atoms.

It has been found that the microemulsions according to the invention are formed particularly easily where a dialkyl ether containing a total of 12 to 24 carbon atoms is present in a quantity of at least 0.5% by weight as solvent for the agrochemicals. A mixture of a dialkyl ether containing a total of 12 to 24 carbon atoms and a monohydric primary alcohol containing 12 to 36 carbon atoms is an even better solvent.

Suitable dialkyl ethers are, in particular, those containing linear primary alkyl groups each having 6 to 12 carbon atoms, more particularly the symmetrical di-n-alkyl ethers, for example di-n-octyl ether. Preferred monohydric primary alcohols are liquid, single-branch alcohols such as, for example, 2-hexyl decanol or 2-octyl dodecanol. The dialkyl ether and the alkanol are preferably used in a ratio by weight of 9:1 to 7:3 as solvent.

Other preferred solvents are N,N-dimethyl decanoic acid amide and glycerol esters, preferably the monoesters and diesters of glycerol, with $C_{12-22}$ fatty acids, for example glycerol monooleate or dioleate.

The agrochemical concentrates contain the solvent or mixtures of solvents in quantities of preferably 0.1 to 40% by weight. However, concentrates containing 10 to 40% by weight of the solvent are preferred. However, concentrates free from water-insoluble solvents are also possible, depending on the agrochemicals used.

The microemulsions according to the invention contain alkyl (oligo)glycosides corresponding to formula (I):

$$R\text{—}O\text{—}[Z]_x \quad (I)$$

in which R is an alkyl group containing 8 to 22 carbon atoms, Z is a sugar unit containing 5 or 6 carbon atoms and x is a number of 1 to 10, as nonionic emulsifiers. Alkyl (oligo)glycosides, their production and their use as surfactants are known, for example, from DE 19 43 689 A1 and from DE 38 27 543 A1.

So far as the glycoside unit is concerned, both monoglycosides where a sugar unit is attached to the fatty alcohol by a glycoside linkage and oligomeric glycosides with a mean degree of oligomerization of up to about 2 are particularly suitable. The glycoside unit in commercially available alkyl oligoglycosides is a glucoside unit.

The nonionic emulsifiers of the alkyl (oligo)glycoside type are present in the concentrates according to the invention in quantities of preferably 10 to 30% by weight and more preferably 10 to 25% by weight.

The concentrates may also contain anionic surfactants, preferably in quantities of 1 to 10% by weight, as auxiliaries or additives. It has been found that microemulsions containing anionic surfactants based on $C_{10-18}$ fatty alcohol ether sulfates show particularly advantageous properties. Fatty alcohol ether sulfates are obtained by alkoxylation of primary fatty alcohols or oxoalcohols in the presence of basic or acidic catalysts at temperatures of 150 to 200° C. and under pressures of 1 to 10 bar. The fatty alcohol polyglycol ethers formed are then reacted with suitable sulfating agents, for example gaseous $SO_3$, to form the required products. The reaction of the alcohol with the alkoxide produces a polyglycol ether mixture of homologs differing in their degrees of substitution in a distribution which can vary according to the catalyst and the quantity of alkoxide used. A suitable example is sodium lauryl ether sulfate which contains 1 to 10 moles of ethylene oxide units per mole of ether sulfate.

The anionic surfactants may be present in the form of their sodium, potassium or ammonium salts and as soluble salts of organic bases, such as mono-, di- or triethanolamine. The anionic surfactants are preferably present in the form of their sodium or potassium salts, more particularly in the form of their sodium salts.

Other suitable anionic surfactants are, for example, alkyl sulfonates, alkyl sulfates or alkyl benzenesulfonates. Preferred surfactants of the sulfonate type are $C_{9-13}$ alkyl benzenesulfonates, olefin sulfonates, i.e. mixtures of alkene and hydroxyalkane sulfonates, and the disulfonates obtained, for example, from $C_{12-18}$ monoolefins containing a terminal or internal double bond by sulfonation with gaseous sulfur trioxide and subsequent alkaline or acidic hydrolysis of the sulfonation products. Other suitable anionic surfactants are alkane sulfonates obtained from $C_{12-18}$ alkanes, for example by sulfochlorination or sulfoxidation and subsequent hydrolysis or neutralization. The readily biodegradable alkane sulfonates are obtained from $C_{12-18}$ alkanes, for example by sulfochlorination or sulfoxidation and subsequent hydrolysis or neutralization. The sulfonate group is statistically distributed over the entire carbon chain, the secondary alkane sulfonates predominating.

Besides the ingredients described above, the concentrates may contain other typical auxiliaries and additives. These include wetting agents, defoamers, dyes and preservatives, other nonionic and cationic emulsifiers or water-soluble alcohols containing 1 to 6 carbon atoms and also inorganic or organic acids for stabilizing the pH value of the concentrates. The concentrates according to the invention preferably have a pH value of 5.5 to 7.5. Concentrates with a pH value of 6 to 7 are particularly preferred. The pH value is adjusted in particular with polyhydroxycarboxylic acids containing 2 to 6 carbon atoms and 2 to 6 hydroxyl groups, for example citric acid. These optional auxiliaries and additives are generally present in quantities of 0.1 to at most 10% by weight.

The microemulsions according to the invention are distinguished in particular by their stability at low temperatures and by their virtually unlimited dilutability. The emulsions can be diluted, for example, with 1000 times their volume of water without the emulsified oil-soluble agrochemicals coalescing. Deionized water as used in laboratories and production units may be used for dilution. However, the concentrates according to the invention may also be diluted with ordinary tap water which has electrolyte concentrations of 0.001 to 1.0 g/l. Normal anionic electrolytes are chlorides, sulfates, carbonates and hydrogen carbonates. The cations present include, for example, sodium, potassium and magnesium ions and also iron ions. The agrochemical concentrates may be used in undiluted form, but are preferably diluted.

The present invention also relates to a process for the production of ready-to-use preparations containing agrochemicals, an agrochemical concentrate as described in the foregoing being diluted with tap water in a ratio of 1:10 to 1:1000.

The concentrates according to the invention are prepared by methods known from the prior art. The agrochemical is normally first dissolved in a suitable solvent, optionally with heating, and the resulting mixture is then added to an aqueous solution of the other components. The emulsion is then intensively mixed at temperatures of 20 to 80° C. until a stable microemulsion is obtained.

EXAMPLES

Examples of microemulsions according to the invention can be found in Tables 1a and 1b below. The emulsions were prepared by initially dissolving the agrochemicals in the oil phase and then emulsifying the resulting solution with the emulsifiers and auxiliaries in water. The agrochemicals used were the insect repellents Irgasan DP 300, Myacide SP, 3535 and 790 and the herbicide nonanoic acid methyl ester.

The transparency of the emulsions was measured at room temperature with a Metrohm Model 662 optical fiber photometer over an optical distance of 10 mm and at a wavelength of 650 nm. All the emulsions according to the invention were water-clear.

In addition, the emulsions were diluted with tap water in a ratio by weight of 1:10 and 1:1000. The diluted microemulsions were then visually evaluated on a scale of 0 to 4, where 0=clear, 1=slightly bluish opalescence, 2=bluish-white, 3=cloudy, grey and 4=phase separation.

| Ingredients: | |
|---|---|
| APG 220 | $C_{8-10}$ alkyl glucoside with x = 1.5 (Henkel) |
| Texapon N 70 | Lauryl ether sulfate sodium salt ethoxylated with 2.3 parts ethylene oxide (Henkel) |
| Irgasan DP 300 | 2,4,4-trichloro-2-hydroxydiphenyl ether (Ciba-Geigy) |
| Myacide SP | 2,5-dichlorobenzyl alcohol (Boots Biocides Group) |
| Insect repellent 790 | N,N-diethyl caprylic acid amide (Merck) |
| Insect repellent 3535 | 3-(N-n-butyl-N-acetylamino)-propioninc acid methyl ester (Merck) |

TABLE 1a (quantities in % by weight active principle)

| | 1 | 2 | 3 | 4 |
|---|---|---|---|---|
| APG 220 | 32.50 | 32.50 | 31.20 | 30.55 |
| Glycerol monooleate | 6.75 | 7.00 | 7.70 | 7.50 |
| Lauric acid methyl ester | | | 26.40 | 25.90 |
| Nonanoic acid methyl ester | 27.50 | 27.50 | | |
| Irgasan DP 300 | | | 4.00 | 6.00 |
| Citric acid | 0.25 | 0.25 | 0.25 | 0.25 |
| Water | 33.00 | 32.75 | 30.50 | 29.80 |
| Dilutability with water 1:10 | 0 | 0 | 0 | 0 |
| Dilutability with water 1:1000 | 0 | 0 | 0 | 0 |

TABLE 1b (quantities in % by weight active principle)

| | 5 | 6 | 7 | 8 | 9 | 10 |
|---|---|---|---|---|---|---|
| APG 220 | 20.0 | 14.0 | 24.0 | 24.0 | 30.0 | 18.0 |
| N,N-dimethyl decanoic acid amide | 40.0 | 40.0 | 30.0 | 30.0 | | |
| D-n-octyl ether | | | 10.0 | 16.0 | | 3.75 |
| Texapon N 70 | 4.0 | 10.0 | 2.4 | 2.4 | | 4.5 |
| Irgasan DP 300 | | | 6.0 | 6.0 | | |
| Myacide SP | 8.0 | 8.0 | | | | |
| Insect repellent 3535 | | | | | 45.0 | |
| Insect repellent 790 | | | | | | 30.0 |
| Citric acid | 0.4 | 0.3 | 0.5 | 0.5 | 0.3 | 0.3 |
| Water | 27.6 | 27.7 | 27.1 | 21.1 | 52.5 | 43.45 |
| Water dilutability 1:10 | 1 | 1 | 0 | 0 | 0 | 1 |
| Water dilutability 1:1000 | 0 | 0 | 0 | 0 | 0 | 0 |

For comparison, two emulsions C1 and C2 without any alkyl (oligo)glycosides were tested as emulsifiers (Table 2).

These emulsions showed clear phase separation after dilution with water.

TABLE 2

(quantities in % by weight active principle)

| | C1 | C2 |
|---|---|---|
| N,N-dimethyl decanoic acid amide | 40.0 | 30.0 |
| D-n-octyl ether | | 10.0 |
| Texapon N 70 | 24.0 | 24.0 |
| Irgasan DP 300 | | 6.0 |
| Myacide SP | 8.0 | |
| Water | 28.0 | 30.0 |
| Water dilutability 1:10 | 4 | 4 |
| Water dilutability 1:1000 | 3 | 3 |

What is claimed is:

1. An agrochemical microemulsion comprising:
   (a) an alkyl (oligo)glycoside corresponding to formula (I):

R—O—[Z]$_x$     (I)

wherein R is an alkyl group having from 8 to 22 carbon atoms, Z is a sugar unit having from 5 to 6 carbon atoms, and x is a number from 1 to 10; and
   (b) an oil phase comprising:
      (i) an organic water-insoluble solvent selected from the group consisting of N,N-dimethyl amides of $C_{8-22}$ fatty acids, glycerol $C_{8-22}$ fatty acid esters of natural or synthetic origin, dialkyl ether having a total of from 12 to 24 carbon atoms, monohydric primary alcohols having from 12 to 24 carbon atoms, and mixtures thereof; and
      (ii) an agrochemical, and wherein 80% of the microemulsion contains droplets between 10 and 100 nm in size.

2. The microemulsion of claim 1 wherein the oil phase is present in the microemulsion in an amount of from 10 to 50% by weight, based on the weight of the microemulsion.

3. The microemulsion of claim 1 wherein the alkyl (oligo)glycoside is present in the microemulsion in an amount of from 10 to 30% by weight, based on the weight of the microemulsion.

4. The microemulsion of claim 1 wherein the microemulsion further contains from 1 to 10% by weight, based on the weight of the microemulsion, of an anionic surfactant.

5. The microemulsion of claim 4 wherein the anionic surfactant is a $C_{10-18}$ fatty alcohol ether sulfate.

6. The microemulsion of claim 1 wherein the agrochemical is present in the microemulsion in an amount of from 10 to 40% by weight, based on the weight of the oil phase.

7. The microemulsion of claim 1 wherein the organic water-soluble solvent is present in the microemulsion in an amount of from 0.1 to 40% by weight, based on the weight of the oil phase.

8. The microemulsion of claim 1 wherein the microemulsion has a pH value of from 5.5 to 7.5.

9. A ready-to-use agrochemical composition comprising the microemulsion of claim 1 and tap water in a ratio by weight of from 1:10 to 1:1000.

10. A process for treating an agricultural substrate comprising contacting the substrate with a ready-to-use agrochemical composition containing an agrochemical microemulsion and water, wherein the agrochemical microemulsion comprises:
   (a) an alkyl (oligo)glycoside corresponding to formula (I):

R—O—[Z]$_x$     (I)

wherein R is an alkyl group having from 8 to 22 carbon atoms, Z is a sugar unit having from 5 to 6 carbon atoms, and x is a number from 1 to 10; and (b) an oil phase comprising:

(i) an organic water-insoluble solvent selected from the group consisting of N,N-dimethyl amides of $C_{8-22}$ fatty acids, glycerol $C_{8-22}$ fatty acid esters of natural or synthetic origin, dialkyl ether having a total of from 12 to 24 carbon atoms, monohydric primary alcohols having from 12 to 24 carbon atoms, and mixtures thereof; and (ii) an agrochemical, and wherein 80% of the microemulsion contains droplets between 10 and 100 nm in size.

11. The process of claim 10 wherein the oil phase is present in the microemulsion in an amount of from 10 to 50% by weight, based on the weight of the microemulsion.

12. The process of claim 10 wherein the alkyl (oligo) glycoside is present in the microemulsion in an amount of from 10 to 30% by weight, based on the weight of the microemulsion.

13. The process of claim 10 wherein the microemulsion further contains from 1 to 10% by weight, based on the weight of the microemulsion, of an anionic surfactant.

14. The process of claim 13 wherein the anionic surfactant is a $C_{10-18}$ fatty alcohol ether sulfate.

15. The process of claim 10 wherein the agrochemical is present in the microemulsion in an amount of from 10 to 40% by weight, based on the weight of the oil phase.

16. The process of claim 10 wherein the organic water-soluble solvent is present in the microemulsion in an amount of from 0.1 to 40% by weight, based on the weight of the oil phase.

17. The process of claim 10 wherein the microemulsion has a pH value of from 5.5 to 7.5.

18. The process of claim 10 wherein the agrochemical microemulsion and water are present in the composition in a ratio by weight of from 1:10 to 1:1000.

\* \* \* \* \*